US008936023B2

(12) United States Patent
McKinnon et al.

(10) Patent No.: US 8,936,023 B2
(45) Date of Patent: Jan. 20, 2015

(54) RESERVOIR SYSTEM FOR GAS DELIVERY TO A PATIENT

(71) Applicant: Westmed, Inc., Greenwood Village, CO (US)

(72) Inventors: Robert J. McKinnon, Highlands Ranch, CO (US); James Dale Bickley, Tucson, AZ (US)

(73) Assignee: Westmed, Inc., Greenwood Village, CO (US)

( * ) Notice: Subject to any disclaimer, the term of this patent is extended or adjusted under 35 U.S.C. 154(b) by 0 days.

(21) Appl. No.: 13/804,700

(22) Filed: Mar. 14, 2013

(65) Prior Publication Data

US 2013/0192597 A1 Aug. 1, 2013

Related U.S. Application Data

(63) Continuation-in-part of application No. 13/188,793, filed on Jul. 22, 2011, which is a continuation-in-part of application No. 12/688,295, filed on Jan. 15, 2010, now Pat. No. 8,616,200.

(60) Provisional application No. 61/145,318, filed on Jan. 16, 2009.

(51) Int. Cl.
*A61M 15/00* (2006.01)
*A61M 16/00* (2006.01)
(Continued)

(52) U.S. Cl.
CPC ....... *A61M 16/0078* (2013.01); *A61M 16/0488* (2013.01); *A61B 5/087* (2013.01); *A61M 16/14* (2013.01); *A61M 16/12* (2013.01);
(Continued)

(58) Field of Classification Search
CPC .......... A61M 16/104; A61M 16/0078; A61M 16/08; A61M 15/0086; A61M 16/01; A61M 16/18; A61M 2202/064; A61M 16/12; A61M 15/009; A61M 15/0065; A61M 15/00; A61M 2015/008; A61M 2016/0021; A61J 1/10; A61J 1/1475; A61J 1/1406; A61J 2001/201; B29L 2031/7148
USPC .......... 604/408, 332, 338, 339, 262; 128/203.28, 200.14, 203.12
See application file for complete search history.

(56) References Cited

U.S. PATENT DOCUMENTS 2,496,175 A * 1/1950 Perry ............................ 604/335
2,667,167 A * 1/1954 Raiche .......................... 604/339
(Continued)

FOREIGN PATENT DOCUMENTS

GB 293900 7/1928

OTHER PUBLICATIONS

Official Action for U.S. Appl. No. 12/688,295 mailed Mar. 20, 2013, 6 pages.
(Continued)

*Primary Examiner* — Manuel Mendez
(74) *Attorney, Agent, or Firm* — Sheridan Ross P.C.

(57) ABSTRACT

A breathing system is provided that employs a reservoir for holding oxygen or an oxygen and medicine mixture while the patient is not inhaling. The reservoir generally prevents waste and reduces cost and helps prevent the patient from re-inhaling the previously exhaled gases. The reservoir also may include a flange extending from an inlet thereof that allows the reservoir to be positioned in an inverted position.

20 Claims, 11 Drawing Sheets

(51) Int. Cl.

| | |
|---|---|
| *A61M 16/04* | (2006.01) |
| *A61B 5/087* | (2006.01) |
| *A61M 16/14* | (2006.01) |
| *A61M 16/12* | (2006.01) |
| *A61M 16/08* | (2006.01) |
| *A61M 11/06* | (2006.01) |
| *A61M 16/06* | (2006.01) |
| *A61M 16/10* | (2006.01) |
| *A61M 16/20* | (2006.01) |

(52) U.S. Cl.
CPC ........... *A61M16/0875* (2013.01); *A61M 11/06* (2013.01); *A61M 16/0816* (2013.01); *A61M 16/0084* (2014.02); *A61M 16/06* (2013.01); *A61M 16/1055* (2013.01); *A61M 16/208* (2013.01); *A61M 15/0086* (2013.10); *A61M 2202/0208* (2013.01); *A61M 15/0016* (2014.02); *A61M 15/0018* (2014.02); *A61M 16/1065* (2014.02); *A61M 2207/00* (2013.01); *A61M 16/0866* (2014.02); *A61M 16/125* (2014.02)
USPC ..................................................... 128/203.12

(56) References Cited

U.S. PATENT DOCUMENTS

| | | | | |
|---|---|---|---|---|
| 3,039,464 | A | * | 6/1962 | Galindo ........................ 604/344 |
| 3,367,380 | A | * | 2/1968 | Dickey .......................... 383/104 |
| 3,906,996 | A | | 9/1975 | DePass et al. |
| 3,915,212 | A | * | 10/1975 | Bujan et al. ................... 604/408 |
| 3,967,619 | A | | 7/1976 | Story et al. |
| 4,088,131 | A | | 5/1978 | Elam et al. |
| 4,676,239 | A | | 6/1987 | Humphrey |
| 4,823,784 | A | | 4/1989 | Bordoni et al. |
| 5,020,530 | A | | 6/1991 | Miller |
| 5,061,241 | A | | 10/1991 | Stephens, Jr. et al. |
| 5,099,833 | A | | 3/1992 | Michaels |
| 5,613,489 | A | * | 3/1997 | Miller et al. ............. 128/203.28 |
| 5,779,693 | A | | 7/1998 | Ropiak et al. ................. 604/408 |
| 6,578,574 | B1 | * | 6/2003 | Køhnke ..................... 128/203.11 |
| 6,902,551 | B2 | * | 6/2005 | Hansen et al. ................ 604/342 |
| 6,966,904 | B2 | * | 11/2005 | Ruth et al. .................... 604/514 |
| 7,473,246 | B2 | * | 1/2009 | Vancaillie et al. ............. 604/411 |
| 2010/0180891 | A1 | | 7/2010 | McKinnon et al. |
| 2011/0277754 | A1 | | 11/2011 | McKinnon et al. |

OTHER PUBLICATIONS

Official Action for U.S. Appl. No. 12/688,295 mailed Apr. 11, 2013, 9 pages.

* cited by examiner

RESERVOIR SYSTEM FOR GAS DELIVERY TO A PATIENT

CROSS-REFERENCE TO RELATED APPLICATION

This application is a Continuation-In-Part of U.S. patent Ser. No. 13/188,793, filed Jul. 22, 2011, which is a Continuation-In-Part of U.S. patent Ser. No. 12/688,295, filed Jan. 15, 2010, which claims the benefit of U.S. Provisional Application Ser. No. 61/145,318, filed Jan. 16, 2009, the entirety of each application being incorporated by reference herein.

FIELD OF THE INVENTION

Embodiments of the present invention generally relate to a breathing system designed to provide gas, such as an oxygen and medicine mixture, to a patient.

BACKGROUND OF THE INVENTION

Hospitalized patients with pulmonary or cardiovascular health issues often require supplemental oxygen. Typically, supplemental oxygen is delivered to a patient from an oxygen source that is interconnected by tubing to a patient interface, e.g., a mouth piece or a mask. In addition, some patients require medicine, which is delivered to the patient in the form of aerosolized particles mixed with the oxygen by a nebulizer that is interconnected to the tubing and positioned between the oxygen source and the patient interface. "Gas" as used herein shall refer to the mixture of oxygen and medicine. Those of skill in the art will appreciate that the source may deliver compressed air, a mixture of helium and oxygen, or any other substance that is typically used for patient care.

One drawback of prior art breathing systems is that the patient often re-breathes exhaled gas which reduces the amount of medicine-rich gas that would otherwise be received or drawn in by the patient. To avoid this drawback, breathing systems often include an inlet check valve or similar device that prevents exhaled air from intermingling with the incoming or supplied gas. More specifically, the pressure of the exhaled gas is sufficient to close the inlet check valve so that exhaled gas is forced through vents or an outlet port located between the patient and the inlet check valve. Pressure generated by the patient's inhalation opens the inlet check valve which allows the patient to breath in the prescribed gas.

It is another drawback that breathing systems of the prior art often waste medicine. More specifically, the source of many breathing systems continuously output oxygen at a predetermined but variable mass flow rate and pressure. Thus, when the patient is not inhaling, i.e., during exhalation or during the dwell period characterized as the time between inhalation and exhalation, gas continues to be delivered. As a result, the oversupplied gas is vented through the outlet port and/or through mask vents. To account for this decrease in medicine delivery to the patient, health care providers typically increase the amount of medicine added to the incoming oxygen. In an extreme example, a healthcare provider will prescribe three times the required dosage to accommodate losses, which is wasteful and increases healthcare costs. One attempt to solve the problem of waste has been to incorporate a reservoir bag into the gas delivery system to capture the delivered gas when the patient is not inhaling and subsequently deliver the captured gas to the patient upon the next breadth, which reduces the amount of gas vented to atmosphere. When the patient does inhale, the gas stored in the reservoir bag is inhaled along with gas that is being continuously delivered by the supply source.

Often reservoir bags are thick-walled and made of a durable material to withstand damage associated with shipping, handling, and use. Thick-walled construction, however, affects the ability of the bag to inflate and therefore adversely affects the ability of the bag to capture excess gas. It follows that as the pressure required to inflate a thick-walled reservoir is greater than the pressure required to open the inlet check valve, the pressurized gas delivered to the patient during the dwell time will often flow to the mask only to be vented. Stated differently, the inlet check valve of many breathing systems may open without the reservoir bag being filled and the gas will vent to atmosphere through the outlet port or mask vents rather than filling the reservoir.

One ineffective response to this problem is to increase the pressure of the oxygen source, and thus the gas, to ensure the bag inflates. However, increasing the source pressure will amplify the wasteful effect if the reservoir bag does not inflate quickly. That is, the pressure of the system is directly proportional to the gas mass flow rate which in turn is directly proportional to gas losses through the outlet port when the inlet check valve inevitably opens. And, even if the higher pressure gas completely inflates the reservoir bag, eventually the pressure of the incoming gas will urge the inlet check valve open, which allows the gas to vent through the outlet port. As one of skill in the art will appreciate, losses will be greater than those experienced by a system operating at a lower pressure.

Another way to address the medicine waste issue is to vary the size of the opening of the outlet port. U.S. Pat. No. 5,613,489 ("the '489 patent"), which is incorporated herein by reference, is directed to an outlet port comprised of a selectively adjustable orifice that provides adjustable resistance to exhalation. As one of skill in the art will appreciate, the greater the resistance to exhalation, the greater the pressure within the housing, which keeps the inlet check valve closed when the patient exhales and during the dwell time. The adjustable orifice may also be used to control exhalation by producing a positive expiratory pressure (PEP) which enhances patient therapy. The orifice of the exhalation port described in the '489 is adjusted by altering a wedge-shaped opening from about 10 degrees to about 60 degrees. One drawback with this method of controlling exhalation is that a path is always open. Thus, if the system of the '489 patent is used with a self-inflating reservoir, as will be described in detail below, ambient air will be drawn in through the orifice when the patient inhales. That is, patients with poor lung function will not be able to provide enough negative pressure during inhalation to collapse a self-inflating reservoir, which maximizes medicine delivery, without the orifice leaking ambient air.

Reservoir bags of the prior art are often not easy to clean and reuse. Thus many individuals choose to discard reservoir bags, which is wasteful and expensive. In addition, those individuals who decide to clean and reuse their reservoir bags often find it difficult to ensure that all cleaning fluids are expelled from the reservoir bag.

Accordingly, there is a long standing and unresolved need to provide a system for delivering medicine to a patient that efficiently stores a reserve of gas when the patient is not inhaling, thereby eliminating or substantially reducing medicine waste by making the reserve available to the patient when he or she subsequently inhales.

SUMMARY OF THE INVENTION

Embodiments of the present invention provide a gas delivery system with a reservoir wherein internal system pressure requirements are established that ensure that continuously produced and supplied gas is captured by filling or substantially filling a reservoir when the patient is not inhaling. More specifically, one embodiment of the present invention employs an inlet check valve with increased resistance. Further, resistance to opening the inlet check valve may be added to the system, such as by placing a filter, a throttle—which may or may not be variable, decreased diameter tubing, or some other medically inert porous obstruction upstream of an outlet port, which is located between the patient and the inlet check valve. As used herein, "upstream" refers to a position closer to the gas supply and away from the patient. Still further, the wall thickness of the inflatable reservoir may be reduced, which will facilitate inflation by reducing the pressure needed to inflate the reservoir. Each of these solutions, alone or in combination, will capture the continuously-produced and supplied gas such that a reserve is available for the patient, which will reduce waste. The resistance to gas flow occurs before the gas reaches the outlet port of the delivery system. In other words, any structure or component added, altered, or selectively altered for purposes of increasing the internal resistance to gas flow toward the outlet port must not be positioned between a patient interface, i.e., a mouth piece or mask, and the outlet port, otherwise the solution will be ineffective as the gas will vent to atmosphere through the outlet port. Additionally, the internal system pressure may be adjustable relative to the volume and rate of the patient's breath cycle such that the internal system pressure may be set to cause the reservoir to fill or is substantially fill before each inhalation cycle.

It is another aspect of some embodiments of the present invention to provide self-inflating reservoir. More specifically, reservoirs made of a resilient material, such as a shape-memory polymer, are employed that return to their original shape after compression caused by inhalation. The material used by one embodiment is flexible polyvinyl chloride (PVC) or other similar elastomeric materials, such as silicon or styrenic block copolymer (SBC) manufactured by Kraton Performance Polymers Inc. Further, as previously noted, the wall thickness of the contemplated reservoir may be directly proportional to the pressure required to inflate the reservoir. Effective wall thickness is a function of the material selected and may range from about 0.100 mm near the opening of the reservoir to about 0.030 mm in some areas of the primary gas-holding portion. In one embodiment, the wall thickness is consistent from the opening to about the midway point of a spherical reservoir (a first hemi-spherical portion) wherein the remainder of the spherical reservoir from the midway point to the end of the reservoir (the opposed hemispherical portion) is made of a thinner or different material. By defining the reservoir material of manufacture and/or wall thickness, the amount of negative pressure created by the reservoir as it rebounds can be predetermined. Furthermore, the negative pressure assists in filling the reservoir and assists in keeping the inlet check valve closed during patient exhalation and dwell time.

It is also noted that patients frequently do not breathe as deeply as they should following many medical procedures. To resolve this, doctors will prescribe the use of incentive spirometer which gives the patient and doctor a visual indication that they are breathing deeply. The shape-memory reservoir of some embodiments of the invention will also provide such visual feedback to the patient and the patient's doctor or attendant. More specifically, it is yet another aspect of the present invention to provide a somewhat stiff but resilient reservoir that will resist inhalation, which is a helpful therapy tool. More specifically, inhalation of gas from a reservoir of a contemplated embodiment of the present invention will take more patient effort. Increased effort translates into a deeper breath that will force medication deeper into the patient's lungs. Forcing the patient to breathe deeper has the added benefit of preventing pneumonia as deep breaths necessarily help prevent fluid build-up in the patient's lungs. Further, by monitoring the degree of inhalation by the patient through observation of the shape of the reservoir during patient inhalation and exhalation (e.g., the reservoir expanding on exhalation and collapsing or contracting to a degree during inhalation), the drug administration process may be similarly monitored, and as such the reservoir provides biofeedback to the patient and/or the patient's attendant regarding the patient's breathing pattern.

It is another aspect of the present invention to provide a reservoir that collapses in a controlled fashion to ensure that the gas contained in the reservoir is completely expelled. Bag reservoirs of the prior art can collapse in such a way to block the reservoir opening and thereby trap some gas inside the reservoir. Thus, reservoirs of some embodiments of the present invention employ thicker and stiffer walls adjacent to the open end than the gas-holding portion of the reservoir to prevent the collapsing reservoir from blocking the open end and trapping gas. Other reservoirs employ stiffening ribs or seams that help control reservoir collapse to prevent blocking the opening. Still other reservoirs of the contemplated invention are made of a combination of materials that collapse in a predetermined manner. For example, in one embodiment the reservoir is made of two distinct materials, one stiff and less apt to collapse than the other. In operation, the more flexible material, which is located away from the reservoir opening, will collapse first. Any of these reservoir configurations and those similar thereto has the advantage of maintaining the opening while having the primary gas-holding portion fully collapse upon inhalation, which allows substantially all of the stored gas to be inhaled. Alternatively, the reservoir opening may be held open with an adapter that is inserted into the opening.

It is a related aspect of the present invention that condensation, which contains medicine, in the reservoir is reduced. More specifically, collapsed walls of prior art reservoir bags may stick together and trap gas within folds, creases, or pockets which leaves medication adhered to the inside surface of the bag. A test of one embodiment of the present invention reduced the amount of condensation in the reservoir by 90%.

It is yet another aspect of the present invention to provide a breathing system, comprising: a gas source; a housing having: a first inlet in fluid communication with said gas source, a first port in fluid communication with a patient interface, and a second port in fluid communication with a reservoir; an outlet, wherein said housing includes a first check valve positioned between said first inlet and said outlet; and wherein output from said gas source flows to said first inlet and to said reservoir, the output inflating said reservoir until said first check valve is opened, which allows the output to be directed from said reservoir and said gas source to said patient interface.

It is another aspect of the present invention to provide a method of reducing waste in the delivery of aerosolized medicine or gas to a patient comprising: providing a gas source; providing a housing having: a first port associated with said gas source, a second port associated with a reservoir, a third port associated with a patient interface, and a fourth port, and a check valve positioned between said first port and said fourth port; delivering a gas from said gas source to said first port of said housing; directing said gas to said reservoir via said second port; opening said check valve upon patient inhalation; directing said gas from said reservoir to said patient interface; closing said check valve when the patient is not inhaling; and directing exhaled air out of said housing through said fourth port.

It is yet another aspect of embodiments the present invention to provide a reservoir bag that includes a flange extending from its inlet. The flange is used to support the reservoir in an inverted position so that water can exit therefrom which facilitates drying. As some of the reservoir bags contemplated herein are made of soft blow-molded material, stiffening members may be included that help prevent reservoir collapse when inverted. The stiffening members, e.g., ribs, may be integrated into the body of the reservoir bag. For example, the tools used to form the reservoir bag made create thickened areas that act as stiffening members.

While the following disclosure describes the invention in connection with those embodiments presented, one should understand that the invention is not strictly limited to these embodiments. Furthermore, one should understand that the drawings are not necessarily to scale and that in certain instances, the disclosure may not include details that are not necessary for an understanding of the present invention, such as conventional details of fabrication and assembly.

DETAILED DESCRIPTION

Figure 1:
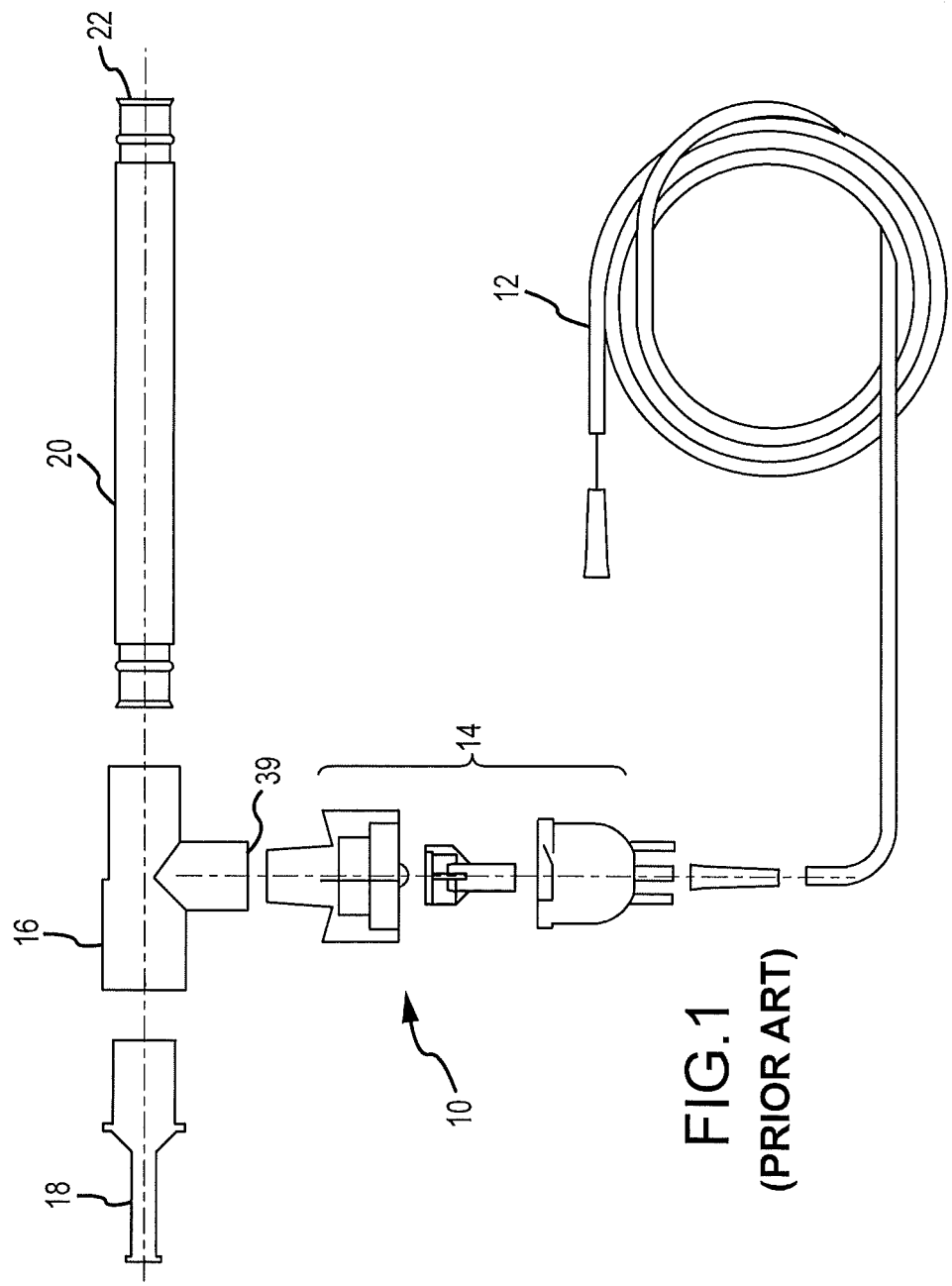
FIG. 1 is an exploded view of one embodiment of a currently available commercial gas delivery system, including a nebulizer.

FIG. 1 is an example of a current commercial aerosol delivery system 10 that does not employ a reservoir bag or one-way valving system. Oxygen flows though supply tubing 12 to the nebulizer 14 that adds medicine to the oxygen to create a gas comprised of aerosolized gas. The gas travels through housing 16 and mouth piece 18 toward the patient, into a tube 20 or both, depending upon the dynamic internal system pressures. The mouth piece 18 may be replaced by a mask 14 as shown in FIG. 4. The tube 20 may act as a reservoir wherein inhalation will draw gas from the tube 20, through the housing 16 and to the mouth piece 18 as well as from the nebulizer 14. Upon exhalation, the exhaled gases flow out through the mouth piece 18 and housing 16 into the tube 20 and ultimately into atmosphere through outlet port 22 of the tube 20. During any period of time when the patient is not inhaling, the aerosol mixture from the nebulizer 14 will flow toward the mouth piece 18 and toward the outlet port 22. The portion of the gas that flows toward the outlet port 22 will purge at least some of the exhaled $CO_2$ that may reside in the tube 20. However, if adequate flow sufficient to achieve a complete purge of $CO_2$ from the tube 20 is not provided, the patient may re-breathe the $CO_2$ residing in the tube 20 upon subsequent inhalation. In addition, using incoming gas to purge exhalation gases wastes medication and reduces the prescribed volume of medication that is intended for the patient, thereby requiring the dosage to be increased due to system waste.

Turning to FIGS. 2 and 3, a pulmonary drug delivery system 30 is shown. In general terms, the pulmonary drug delivery system 30 comprises a housing 32 having a patient interface port 33, which may be customized to be the interface with a patient via a mouth piece 34 or a mask. The housing 32 also possesses a reservoir port 36 and a nebulizer port 39 associated with the main housing 32. A nebulizer 38 is associated with the nebulizer port 39 and an oxygen source 40 by way of tubing 42. Further, an inflatable/deflatable reservoir 44 associated with the main housing at the reservoir port 36. The oxygen source 40 may be a self-contained oxygen tank, a hospital's own oxygen source, including an oxygen generating device, a source of ambient air, a blender or manifold that is connected to a combination of sources, an oxygen concentrator, and a compressor, for example. A connector 46 may be used to interconnect the reservoir 44 to the main housing 32, and a band 48 or tape provides one option of sealing the reservoir 44 to the connector 46. An oxygen line 42 is attached between the nebulizer 38 and the oxygen source 40. The nebulizer receives a continuous supply of oxygen from the source 40 and mixes the oxygen with aerosolizes medicine to form a gas for inhalation by the patient. An inlet check valve 50 is installed in the main housing 32 that opens upon inhalation, thereby allowing gas to be drawn in by the patient by the mouth piece 34. The valve 50 also prevents exhaled gas from flowing to the inflatable reservoir 44. A seat (see FIG. 3, #51) may be formed in the housing 32 upon which the valve 50 is positioned.

The flow rate at which oxygen is supplied to the nebulizer is a known amount and may be adjusted as required. In one embodiment, the pressure being delivered by the source is greater than the pressure required to open the inlet check valve 50, but the flow rate of the pressurized oxygen is decreased so that it takes some time for the pressure in the reservoir 44 and housing 32 to reach a level that would open the inlet check valve 50. Accordingly, when a patient is not inhaling, the gas exiting nebulizer 38 will accumulate in the reservoir. At some point, however, the inlet check valve 50 will open due to the pressure build up in the housing 32 and the reservoir 44, if the valve is not otherwise opened by the patient's inhalation. Upon inhalation, the valve will open or remain open and allow the patient to receive the gas from the nebulizer 38, as well as the supply of gas contained in the reservoir 44. If the patient is not inhaling at this time, the excess gas will vent through port 52 and PEP valve 53.

The flow rate of the gas from the nebulizer 38 should be adjusted to correspond with the patient's inhalation such that the volume of gas that accumulates in the reservoir matches or nearly matches the patient's inhalation volume intake, accounting for the volume of gas that would also be simultaneously supplied from the nebulizer. Should the patient overbreathe and deplete the volume of gas in the reservoir, the patient may still inhale the gas being generated by the nebulizer as well as ambient air drawn through an outlet 52 or Positive Expiratory Pressure (PEP) valve 53. When the patient exhales the inlet check valve 50 will close and all exhaled gas will exit through the outlet 52 or the PEP valve 53. One of skill in the art will appreciate that the exhaled gas also may exit though another outlet integrated into the housing 32, the mouth piece 34, the mask (if applicable), etc. That is, the PEP valve 53 is not necessarily required for the contemplated invention to function. The PEP valve 53 may employ a member 56 that is selectively adjusted to control the flow of fluid therethrough. In one embodiment the PEP valve 53 is used in conjunction with a filter mechanism 54 to filter exhaled gases, remove contaminants, bacteria, viruses and other contaminates for the safety of healthcare workers and others attending to the needs of the patient. During exhalation and any pause before the next inhalation, the gas will inflate the reservoir 44.

To ensure gas is not wasted when the patient is not inhaling and to ensure the reservoir 44 fills, even in the case of patients requiring high oxygen flow rates, which generate higher internal pressures that could cause the inlet check valve 50 to open at times other then when the patient is inhaling, the resistance of the inlet check valve 50 may be increased. In one embodiment, a manually adjustable spring is used to alter the resistance of the valve 50. Alternatively, a second check valve of increased resistance (not shown) may be placed in the delivery system upstream between the PEP valve 53 and inlet check valve 50. This second valve would compensate for situations where the inlet check valve 50 would otherwise open at times other than during patient inhalation. Further, and by way of example, resistance could take the form of one or more filters, some type of inert or non-harmful but porous obstruction, a throttle in the tubing, a throttle in the housing 32, a circuitous air path, a flow path comprising flexible walls that expand and contract with pressure changes, tubing with integrated pressure relief characteristics (i.e., a hole covered by a flexible member that allows gas to escape when the pressure of the gas reaches a predetermined level), or a combination of one or more of these options. An important feature is that the internal resistance to gas flow toward the mouth piece upstream of the PEP valve 53 is greater than that required to fill the reservoir bag 44.

Figure 3:
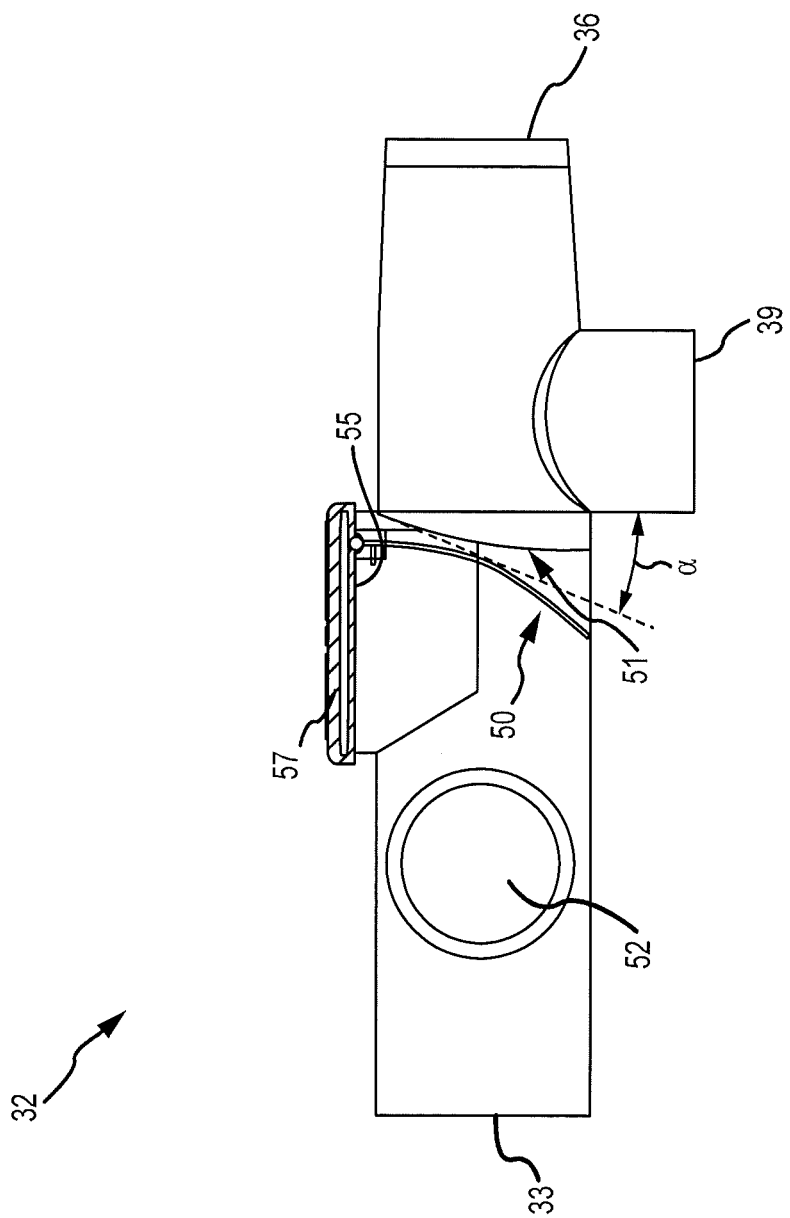
FIG. 3 is a housing employed by some embodiments of the present invention.

Referring now to FIG. 3, the housing 32 of one embodiment of the present invention is shown that includes a patient interface port 33, a nebulizer port 39 and a reservoir port 36. The housing 32 also includes the outlet 52 that is adapted to interconnect with the PEP device. The valve 50 is integrated into the housing 32 via an opening 55 in a portion of the housing 32. A cap 57 is also integrated to the opening to seal the housing 32. The valve 50 rests against a valve seat 51, which may be angled ($\alpha$). The valve seat 51 will alter the pressure required to open the valve 50 as a function of angle ($\alpha$). More specifically, if the valve is positioned vertically as shown, it will require less pressure to open if it is angled, for example, about 30 degrees, wherein the weight of the valve 50 must be additionally overcome to open the same.

Figure 4:
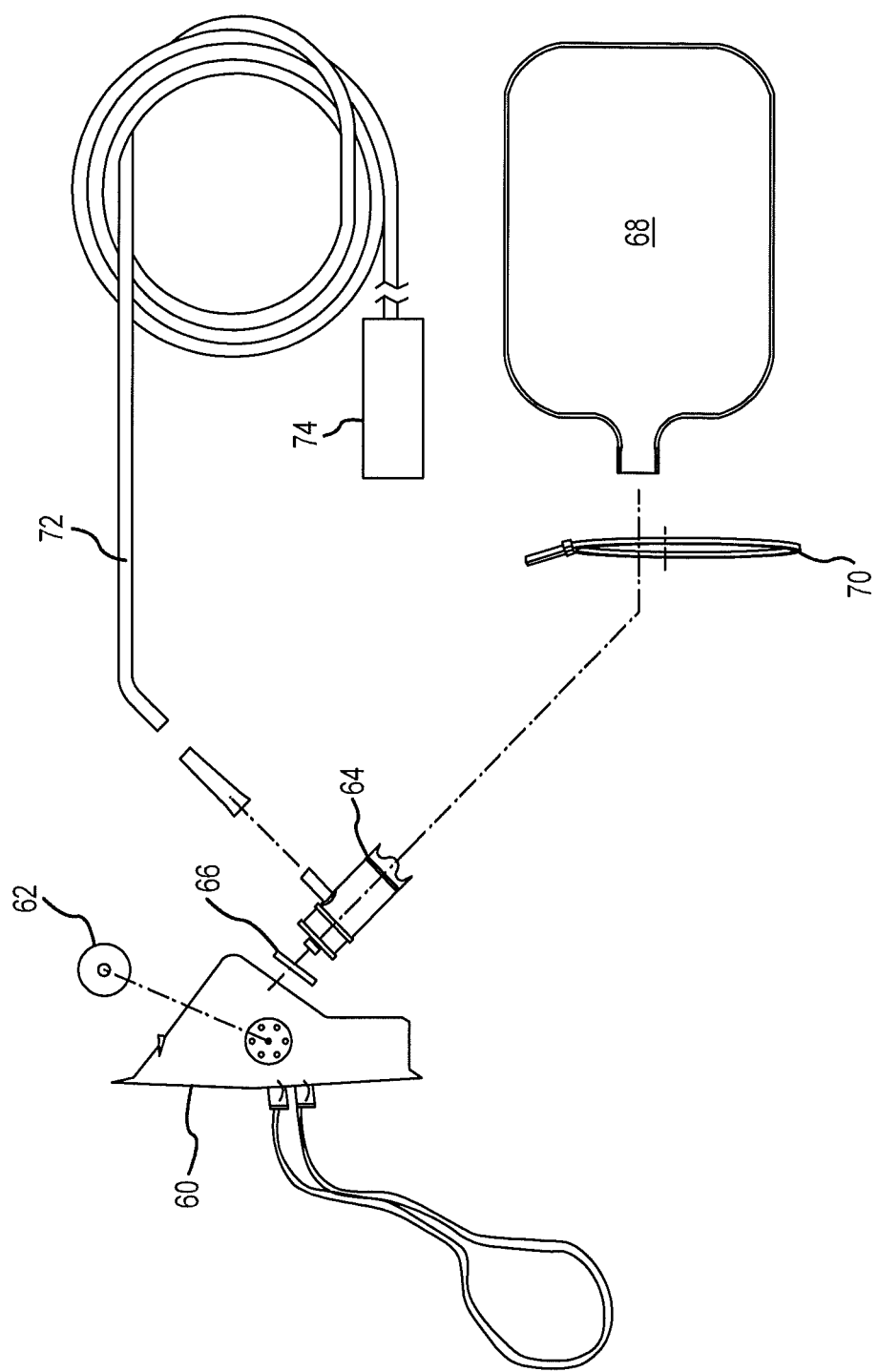
FIG. 4 is an exploded view of an alternative embodiment of the present invention, without a nebulizer.

FIG. 4 illustrates a non re-breather mask system incorporating an embodiment of the present invention. A patient mask 60 may have one or more outlet check valves 62 that prevents ambient air from entering. Alternatively, the mask 60 may have exit vents that are not valves or the exhalation may simply escape around the peripheral edges of the mask. A housing 64 also includes an inlet check valve 66 installed to prevent exhaled gas from entering a reservoir bag 68. As described above, the force needed to open the inlet check valve 66 may be increased to facilitate filling of the reservoir bag 68. The reservoir bag 68 may be attached to the housing 64 with an attaching device 70 such as a band tie or tape. The housing 64 also is interconnected to an oxygen line 72 that is also associated with an oxygen or ambient air source 74.

When the oxygen source is turned on, pressurized oxygen will fill the reservoir bag 68 until the patient inhales. On inhalation, the valve 66 opens and valve(s) 62 close causing all of the inhaled gases to come from the oxygen supply 74 and/or the reservoir 68. The flow of oxygen may be adjusted to meet the patient's requirements. On exhalation, valve 66 closes and valve(s) 62 open to allow the exhaled gas to escape from the mask and the reservoir bag 68 to refill with oxygen. A nebulizer (not shown) may be added between the housing 64 and the oxygen supply line 72 and the system will work in the same way but the reservoir and patient will be provided with an aerosolized mixture of oxygen and medicine or ambient air and medicine.

With the current state of the art non-re-breather mask systems, the reservoir bag is stiff, as described above, and in order to fill the reservoir bag when the patient is not inhaling the pressure from the oxygen supply must be sufficiently large. However, the increased pressure also causes outlet valves 62 and 66 to open causing at least some of the oxygen or aerosol mixture to exit out to atmosphere when the patient is not inhaling. Oxygen or aerosol mixture is thus wasted and the quantity of medicine or oxygen must be increased to accommodate the loss and to ensure the patient receives the prescribed amount of medicine.

Figure 2:
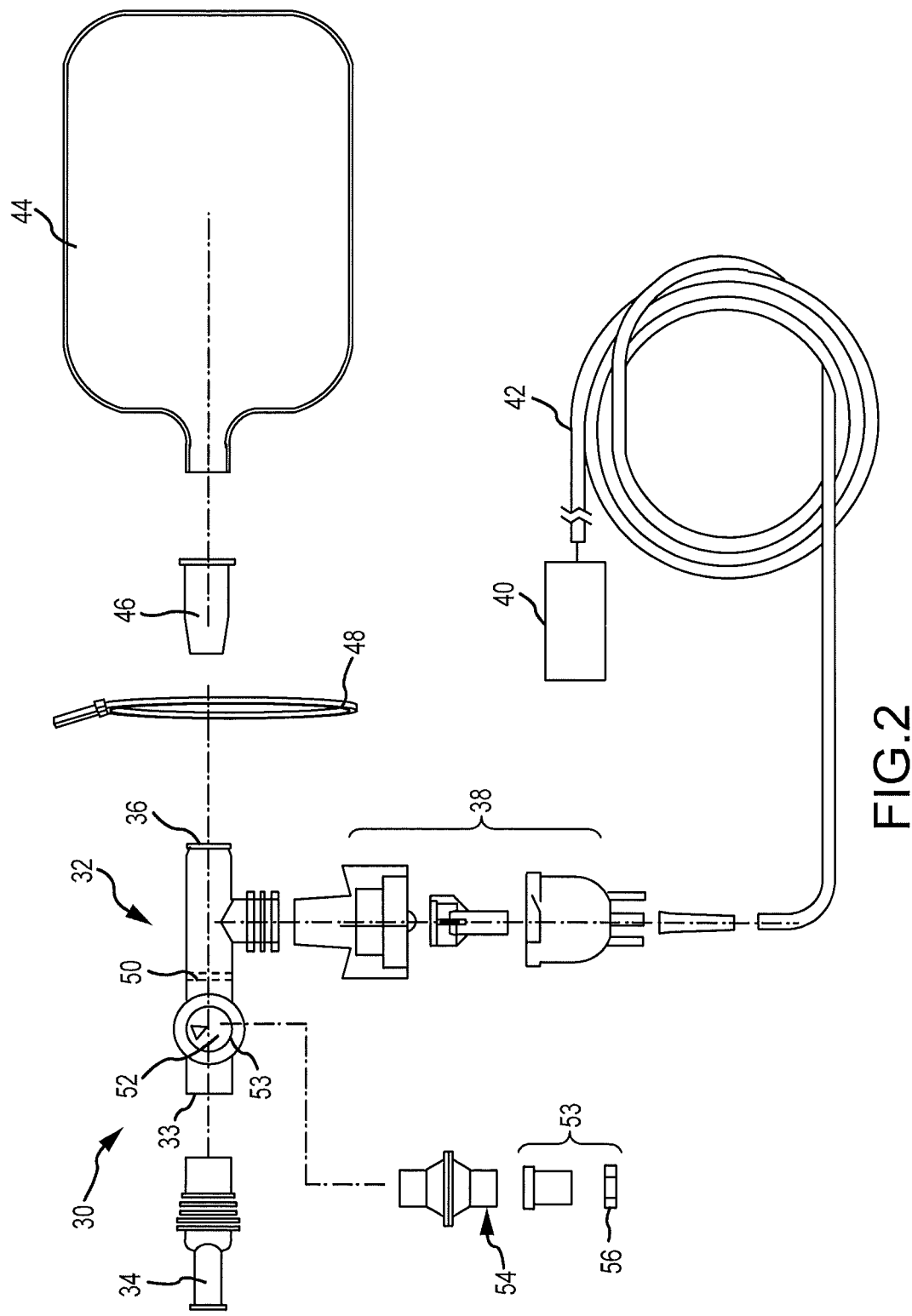
FIG. 2 is an exploded view of a first embodiment of the present invention, including a nebulizer.

In one embodiment of the present invention the pressure required to open valve 66 is adjusted to require a pressure greater than the pressure required to substantially fill the reservoir 68 but is less than the pressure needed to open the valve 66 when the patient inhales. This assures the patient receives the prescribed oxygen level, requires less oxygen flow to achieve the prescribed oxygen levels and reduces or eliminates the loss of oxygen or the aerosol mixture. The system of FIG. 4 may also utilize the methods for adjusting system pressures described above in connection with FIG. 2.

Some embodiments of the present invention employ a semi-rigid, i.e., flexible reservoir. For example, the reservoir may be comprised at least partially of a material that reacts to a negative pressure associated with inhalation but maintains a predetermined shape when not exposed to a pressure variation. This "memory-shape" or "self-inflating" reservoir will thus return to its static or original shape in the absence of external or internal pressure, similar to the bulb of an eyedropper, an aspirator, etc. The material of manufacture of the contemplated reservoir is any number of shape-memory or flexible plastics, for example, flexible PVC of a relatively thin wall thickness in the range of 0.005-0.015 mm. As one of skill in the art will appreciate the contemplated wall thickness would require adjustment depending on the material used. That is, the thicker the material the more memory the part would possess but the less likely it would collapse during inhalation. In addition, if the wall thickness is too thin it would not have enough rigidity to be self inflating. One of skill in the art will appreciate that the reservoir can be substantially rigid but includes a flexible portion that allows expansion or contraction of the flexible portion in response to patient breathing.

The contemplated reservoir would facilitate cleaning or sanitation thereof as it will substantially maintain its shape when disconnected from the system as the opening associated therewith may be oriented to allow drainage of cleaning fluid. This aspect has an advantage over a substantially collapsible, less rigid bag that would prevent the escape of moisture, thereby promoting bacteria and or mold growth which reduces the life expectancy thereof.

Figure 5:
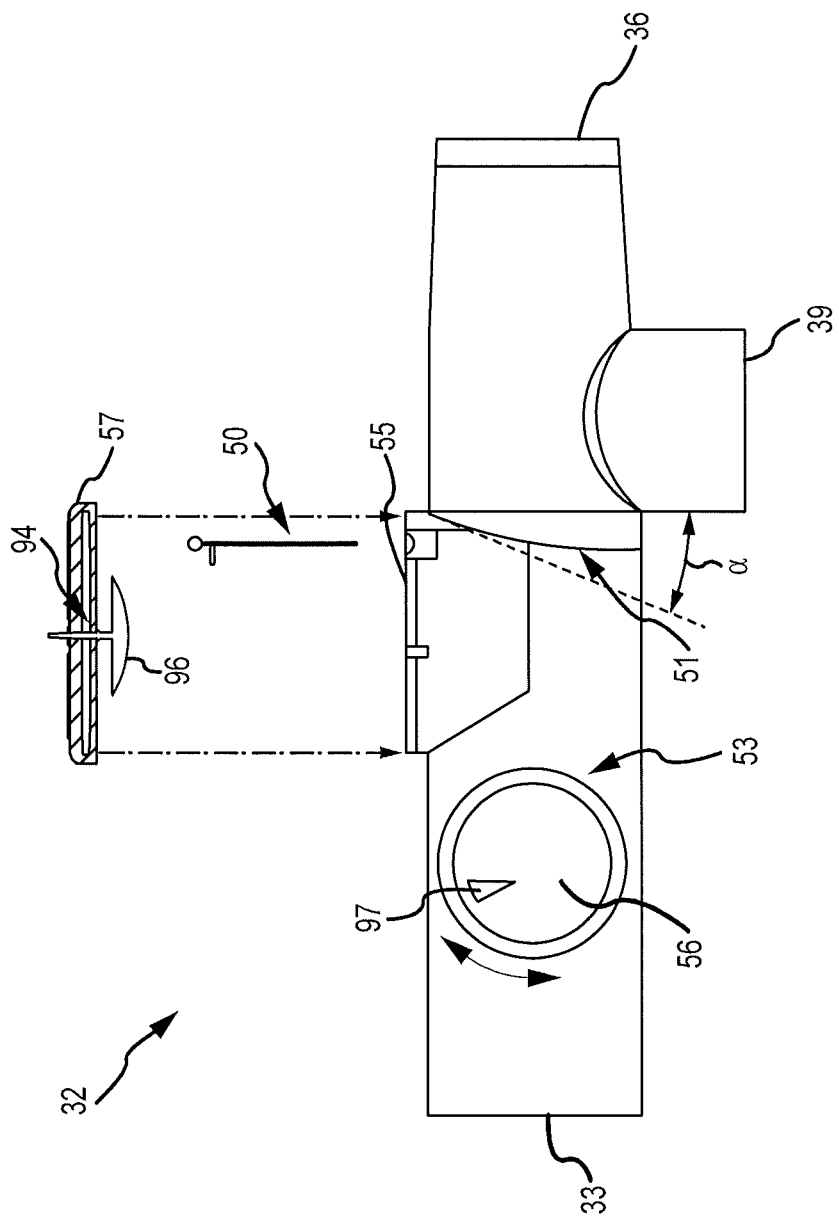
FIG. 5 is an exploded view of a housing employed by another embodiment of the present invention.
Figure 6:
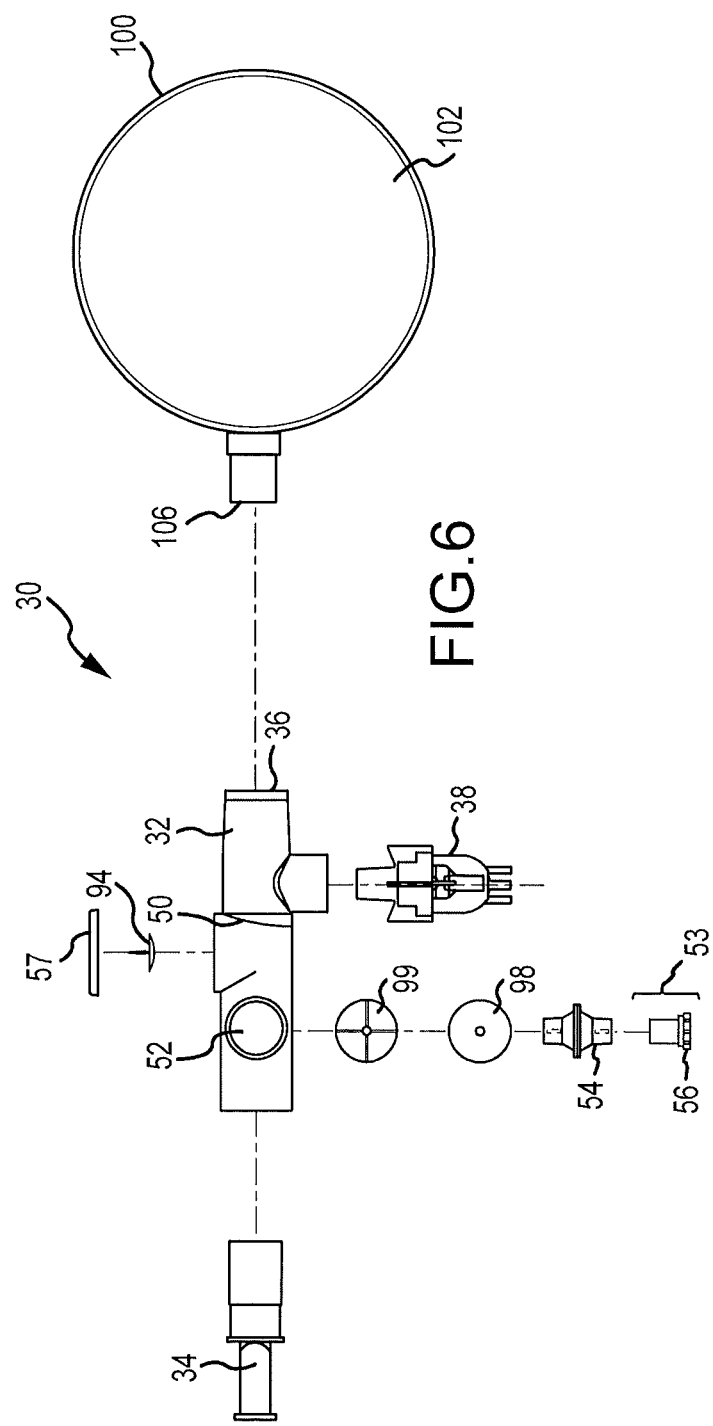
FIG. 6 is an exploded view of a breathing system that employs the housing of FIG. 5.

FIGS. 5 and 6 shows a housing of another embodiment of the present invention that is similar to that described above with respect to FIG. 3. This embodiment of the present invention also includes a valve 94 associated with the opening 55 that allows ambient air to be drawn in by a patient who requires an air volume that cannot be met by the supplied gas or that stored in the reservoir. The valve 94 may be an umbrella, a diaphragm, or a butterfly valve. In operation, if inhalation is greater than the volume of the reservoir (not shown) and greater than the amount of gas being delivered through the nebulizer port 39, the valve 94 will open. The valve 94 may include a plurality of holes (see #95, FIG. 9), which may be adjustable and which will dictate the negative pressure needed to open the valve 94. If an umbrella valve is employed, the thickness of the valve dome 96, the material of manufacture, the valve preload, along with the presence or absence of holes 95, will dictate the negative pressure required for opening. By increasing the pressure required to open the valve 94, important resistance to inhalation is provided. The housing thus forces the patient to draw in air from outside the system when the reservoir is depleted.

The housing of this embodiment of the present invention also includes outlet PEP valve 53 associated with the outlet 52 similar to that shown and described in U.S. Pat. No. 5,613,489, which employs an orifice 97 that may be selectively adjusted by rotating a member 56 to control the amount of exhaled air exiting the orifice 97. More specifically, by reducing the size of the orifice 97, the patient will have to exhale more vigorously to accomplish a full and complete exhalation cycle. The orifice 97 of this embodiment is associated with an outlet check valve 98 that does not allow ambient air to "leak" into the system when the patient inhales and adds little or no resistance to exhalation. Other embodiments of the present invention omit the valve 94 and only employ the outlet check valve 98. The outlet check valve 98 may be a diaphragm or butterfly valve that is associated with a valve retainer 99 interconnected to the outlet 52. Further, the valve 98 can be used in conjunction with an existing variable resistor, if needed.

Figure 7:
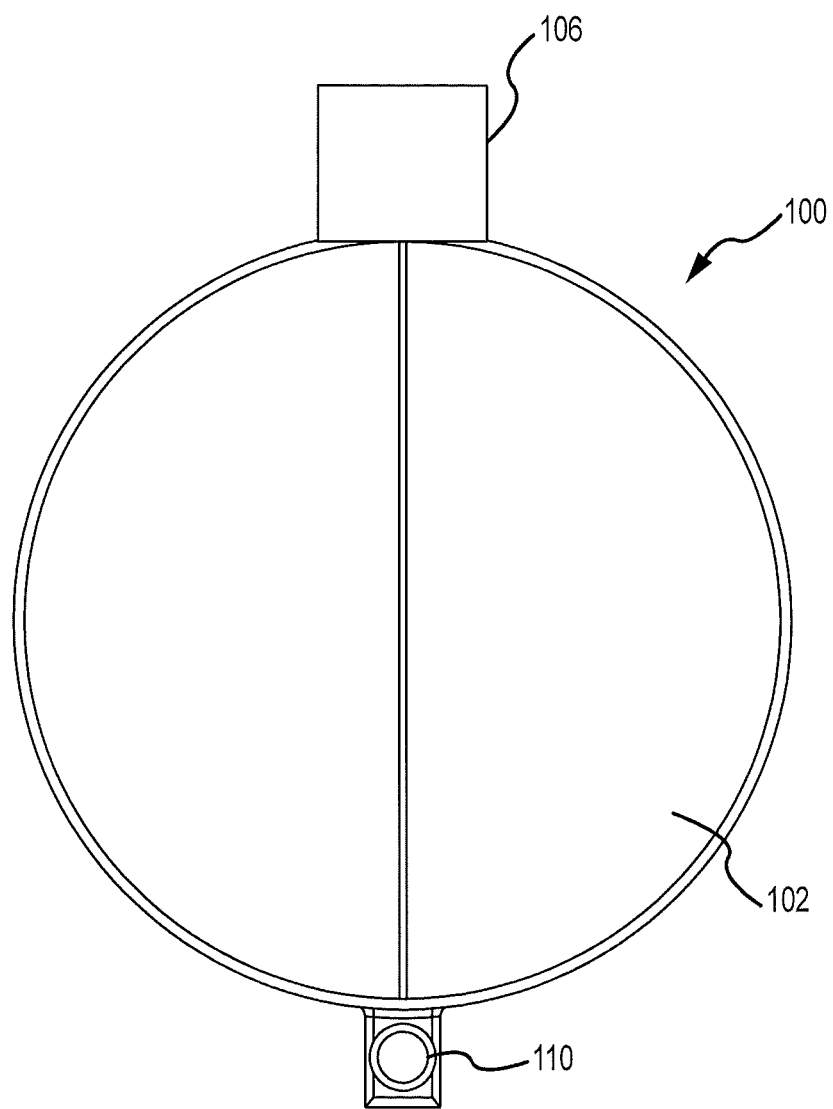
FIG. 7 is an elevation view of a self-inflating reservoir of one embodiment of the present invention.

Referring now particularly to FIGS. 6 and 7 a breathing system 30 that employs self inflating reservoir 100 is shown. The reservoir 100 returns to its original shape when not exposed to a negative internal pressure. The wall thickness of the reservoir and the material of manufacture dictate how the reservoir will rebound. The reservoir 100 requires a sufficient amount of inhalation pressure to collapse and expel the stored gas. Once inhalation has ceased, the reservoir 100 will attempt to rebound to its normal state as the nebulizer refills the volume of the reservoir, thereby ensuring that a sufficient volume is provided to receive incoming gas which will be taken in by the patient's next breath. The reservoir 100 in one embodiment of the present invention has spherical body 102 and an inlet 106 that interconnects to the housing. Further, the reservoir 100 may have a ring 110 that is used to hang the reservoir 100 in a downward facing orientation that facilitates drying.

Figure 8:
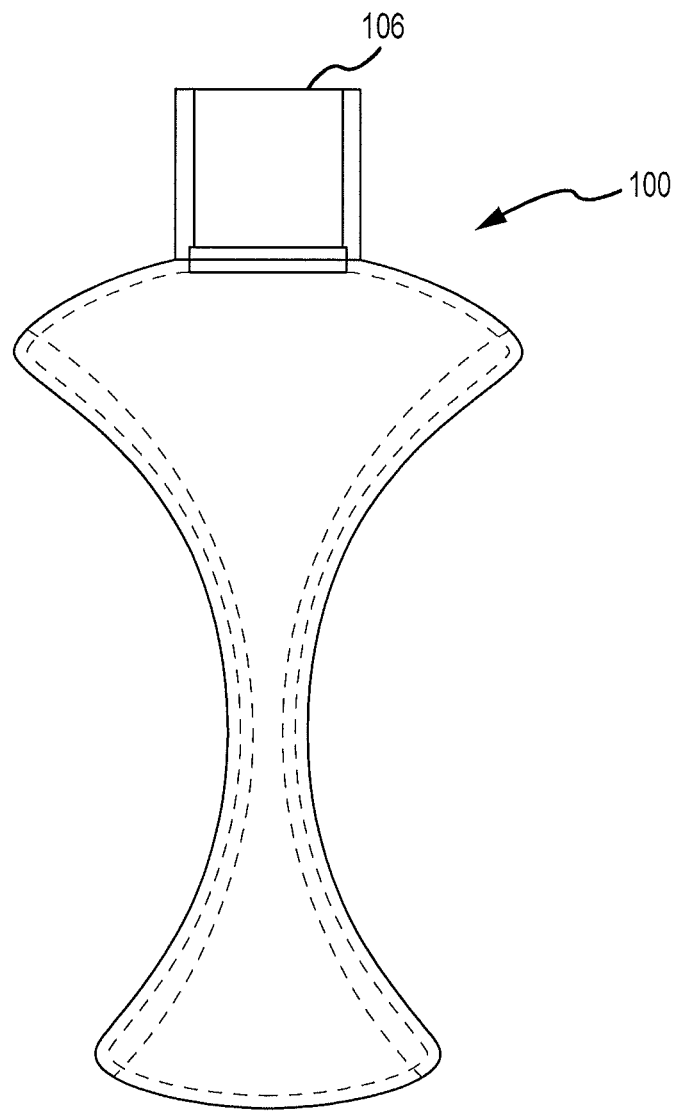
FIG. 8 is an elevation view of FIG. 7 shown in a collapsed state.

FIG. 8 shows a reservoir 100 of one embodiment in a collapsed state. Here, one of skill in the art will appreciate that the area around the reservoir opening 106 remains unobstructed by the collapsed reservoir. This aspect of the present invention allows for a greater amount of gas to be expelled from the reservoir 100 when the patient inhales. FIG. 8 also illustrates that the material composition of the reservoir may be customized such that some portions are more flexible, i.e. collapsible, than others.

Figure 9:
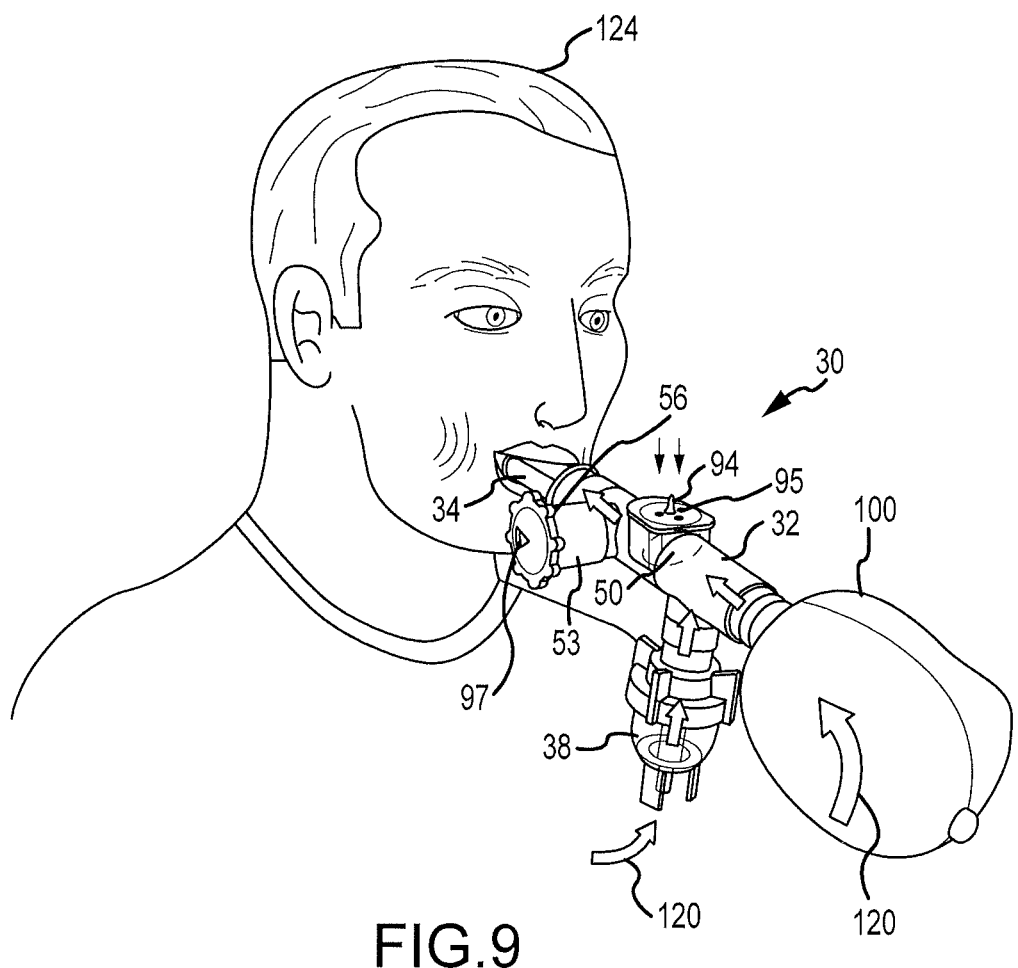
FIG. 9 is a perspective view of the breathing system of FIG. 6 showing a patient inhaling through a mouth piece.
Figure 10:
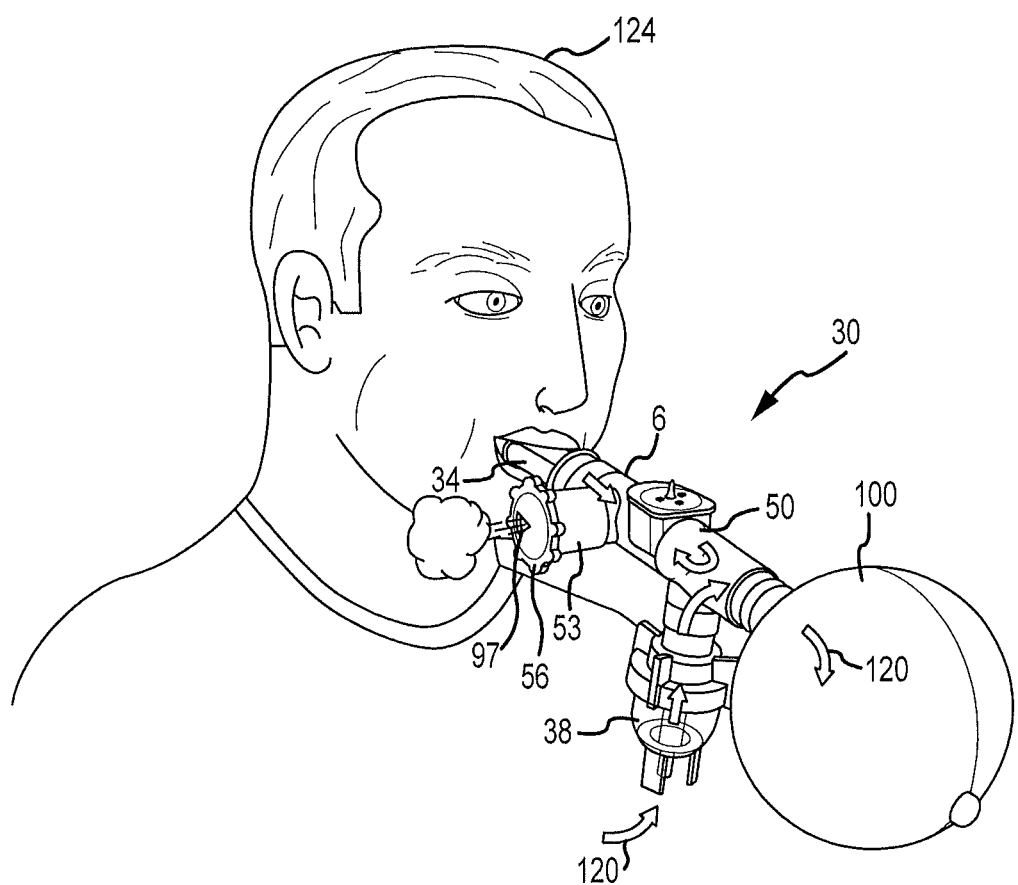
FIG. 10 is a perspective view of the breathing system of FIG. 8 showing a patient exhaling

A typical inhalation/exhalation cycle is shown in FIGS. 9 and 10. As shown in FIG. 9, gas 120 will be drawn into a housing 32 when the patient 124 inhales. The negative pressure associated with inhalation will open the inlet check valve 50 to allow gas from the reservoir 100 to be taken in by the patient 124, which collapses the reservoir 100, as well as from the supply 120. When the patient 124 exhales (FIG. 10), the valve 50 will close and the exhaled gas will exit the housing through the orifice 97. During exhalation and the dwell period, gas will be prevented from reaching the patient by the inlet check valve 50 and the reservoir 100 will fill, which returns the reservoir 100 to its normal shape (assuming the internal system pressure is not greater than the inlet check valve 50 opening pressure). The resilient nature of the reservoir will also help return it to its normal state, which creates a negative pressure that keeps the valve 50 closed when the patient is not inhaling. When the patient inhales again the valve 50 will open and the gas will be initially drawn resistance-free from the reservoir 100 and from the oxygen supply line. Once the oxygen is sufficiently depleted from the reservoir 100, the reservoir 100 will start to collapse similar to that shown in FIG. 8. This resistance to inhalation in some cases is desirable to help a patient take in medicine to a greater degree.

A test of one embodiment of the present invention was performed using a nebulizer and a self-inflating, shape memory, reservoir. A respiratory pump was used to represent the inhalation and exhalation of a patient that was able to provide 500 ml per breath, and inhalation to exhalation ration of 1:1 at fifteen breaths per minute. A high efficiency particulate air (HEPA) filter, which represented the patient, was placed between the respiratory pump and the nebulizer. The HEPA filter, nebulizer, and the body of the self inflating reservoir were weighed prior to testing. Further, 3 ccs of sterile saline were placed in a bowl of the nebulizer and a nebulizer was weighed again. To commence the test, the respiratory pump was switched on and the flow of nebulizer was set to about 8 liters per minute. The system was allowed to function until the nebulizer sputtered, which indicated that nearly all of the sterile saline (representing medicine) was completely administered. All the components were then weighed and the amount of weight loss of the nebulizer was compared to the weight gain of the other parts of the system. The self-inflating reservoir of some embodiments of the present invention gained less than 1% of weight, which is attributed to the nebulized solution, i.e., trapped medicine. For comparison, the systems of the prior art that use a reservoir bag were tested. Such systems yielded residual condensation in the bag (trapped medicine) greater than 10% of the total fluid nebulized. By reducing the amount of condensation occurring inside the reservoir, costs are reduced and the amount of medicine reaching the patient is idealized.

Figure 11:
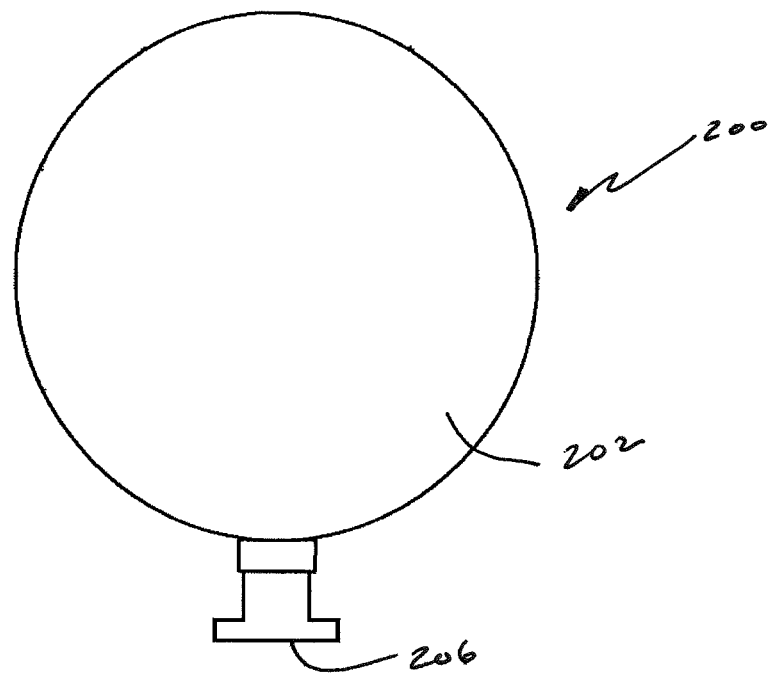
FIG. 11 is a front elevation view of the reservoir of another embodiment of the present invention.
Figure 12:
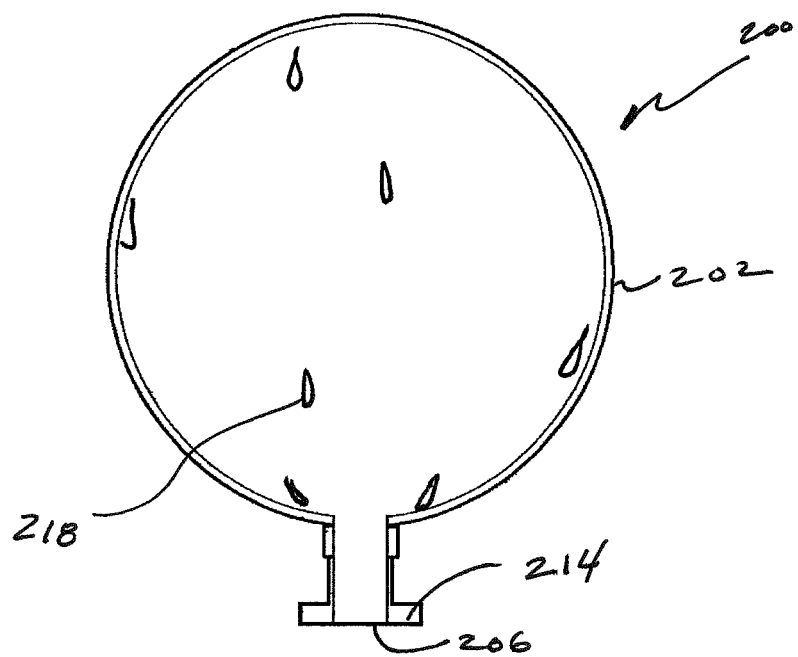
FIG. 12 is a cross-sectional view of FIG. 11.

FIGS. 11 and 12 show a reservoir of another embodiment of the present invention. The reservoir 200 is comprised of a body 202 that is associated with elongated member that ends at an inlet 206. Further, the inlet includes an extended flange 214 extending therefrom. In operation, the reservoir 200 is inverted and rests on the flange 214 to facilitate the egress of water to 18 therefrom. As one of skill in the art will appreciate, the reservoir may be made out of a thin flow-molded material that may collapse under its own weight. Accordingly, some embodiments of the present invention includes stiffening members integrated into the body 202 that sure that the reservoir remains generally expanded while drying.

The present invention, in various embodiments, includes components, methods, processes, systems and/or apparatus substantially as depicted and described herein, including various embodiments, sub combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations, combinations, and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A reservoir for a breathing system, comprising:
   a body;
   a tube extending therefrom, said tube having a first end interconnected to said body and a second end; and
   a flange extending from said second end;
   wherein said reservoir is interconnected to a conduit that leads to an exhalation port of a patient mouth piece; and
   wherein said conduit includes a one-way check valve positioned that creates resistance to gas flow between said reservoir and said exhalation port that is greater than resistance associated with filling said reservoir with gas, said check valve associated with a valve seat that is angled with respect to a longitudinal axis of said conduit.

2. The device of claim 1, wherein said reservoir is made of a blow-molded material.

3. The device of claim 1, wherein said body includes a means for stiffening.

4. The device of claim 3, wherein said means for stiffening are ribs integrated into said body.

5. The device of claim 1, wherein said body includes thickened areas that function to stiffen said reservoir when it is inverted and resting on said flange.

6. The system of claim 1, further comprising a spring associated with said one-way valve for changing the resistance of said one-way check valve.

7. A gas delivery system, comprising:
   an oxygen source;
   a housing having an inlet, a first outlet, a second outlet and a third outlet, said housing including a valve that defines a first volume within said housing between said valve and a patient interface, and a second volume between said valve and said inlet, wherein said valve rests on a valve seat that is angled with respect to a longitudinal axis of said housing;
   said patient interface associated with said first outlet of said housing, said valve being selectively openable when a patient inhales through said patient interface;
   a nebulizer associated said inlet of said housing;
   an oxygen supply line associated with said nebulizer and said oxygen source;
   a filter mechanism associated with said second outlet of said housing;
   a reservoir associated with said third outlet of said housing, said reservoir comprising:
      a body;
      a tube extending therefrom, said tube having a first end interconnected to said body and a second end; and
      a flange extending from said second end; and
   wherein said housing receives a mixture of oxygen and medicine from said nebulizer that is directed to said reservoir, the mixture inflating said reservoir until said valve is opened, thereby allowing the mixture from said nebulizer and said reservoir to exit a first opening.

8. The gas delivery system of claim 7, wherein said patient interface is at least one of a mouth piece or a mask.

9. A breathing system, comprising:
   a gas source;
   a housing having:
      a first inlet in fluid communication with said gas source,
      a first port in fluid communication with a patient interface, and
      a second port in fluid communication with a reservoir;
      an outlet;
   said reservoir comprising:
      a body;
      a tube extending therefrom, said tube having a first end interconnected to said body and a second end; and
      a flange extending from said second end;
   wherein said housing includes a first check valve positioned between said first inlet and said outlet;
   wherein output from said gas source flows to said first inlet and to said reservoir, the output inflating said reservoir until said first check valve is opened, which allows the output to be directed from said reservoir and said gas source to said patient interface; and
   wherein said first check valve associated with a valve seat that is angled with respect to a longitudinal axis of said conduit between said reservoir and said outlet.

10. The breathing system of claim 9, further comprising a second inlet that is in fluidic communication with said patient interface.

11. The breathing system of claim 10, wherein said second inlet is in fluidic communication with air outside said housing, said second inlet comprising a second check valve that opens only after the output is substantially depleted from said reservoir.

12. The breathing system of claim 11, wherein said second check valve has a plurality of apertures.

13. The breathing system of claim 11, wherein said second valve is an umbrella valve.

14. The breathing system of claim 9, wherein said outlet is associated with an adjustable flow regulator that controls the volume of fluid that passes therethrough.

15. The breathing system of claim 9, further comprising a nebulizer in fluid communication with said gas source and said first inlet of said housing.

16. The breathing system of claim 15, wherein said regulator comprises an orifice and an outlet valve movable between first and second positions to change a size of said orifice, wherein a cross-sectional area of said orifice taken perpendicularly to a flow path through said orifice with said valve in said first position is no more than about 0.3 square inches and wherein said cross-sectional area of said orifice with said valve in said second position is less than said cross-sectional area of said orifice with said valve in said first position.

17. The breathing system of claim 9, further comprising a filter mechanism associated with said second outlet of said housing.

18. The breathing system of claim 9, wherein said patient interface is at least one of a mouth piece or a mask.

19. The breathing system of claim 9, wherein said reservoir includes at least one stiffening rib.

20. The breathing system of claim 9, wherein is said reservoir is collapsible when exposed to an internal negative pressure.

\* \* \* \* \*